United States Patent [19]

Naganuma

[11] Patent Number: 5,615,772
[45] Date of Patent: Apr. 1, 1997

[54] MEDICATION FILLED SYRINGE EQUIPMENT

[75] Inventor: Masateru Naganuma, Kanagawa, Japan

[73] Assignee: Seikagaku Kogyo Kabushiki Kaisha (Seikagaku Corporation), Tokyo, Japan

[21] Appl. No.: 495,624

[22] PCT Filed: Mar. 1, 1994

[86] PCT No.: PCT/JP94/00331

§ 371 Date: Sep. 29, 1995

§ 102(e) Date: Sep. 29, 1995

[87] PCT Pub. No.: WO94/20161

PCT Pub. Date: Sep. 15, 1994

[30] Foreign Application Priority Data

Mar. 2, 1993 [JP] Japan .................. 5-014004 U
Mar. 2, 1993 [JP] Japan .................. 5-066139

[51] Int. Cl.⁶ .................. B65D 85/08; B65D 75/00
[52] U.S. Cl. .................. 206/365; 206/364; 206/497; 604/197; 604/220
[58] Field of Search .................. 206/363–365, 206/438, 497, 570; 604/197, 198, 220, 221

[56] References Cited

U.S. PATENT DOCUMENTS

| | | | |
|---|---|---|---|
| 3,272,322 | 9/1966 | Ogle | 206/365 |
| 3,367,488 | 2/1968 | Hamilton | 206/365 |
| 3,548,824 | 12/1970 | Carr | 128/218 |
| 3,677,247 | 7/1972 | Brown | 206/365 |
| 3,890,971 | 6/1975 | Leeson et al. | 206/365 |
| 3,927,762 | 12/1975 | Zdarsky et al. | 206/45.31 |
| 4,573,973 | 3/1986 | Mezi | 604/197 |
| 4,713,060 | 12/1987 | Riuli | 604/199 |
| 4,747,839 | 5/1988 | Tarello et al. | 602/240 |
| 4,877,132 | 10/1989 | Makris et al. | 206/364 |
| 4,878,903 | 11/1989 | Mueller | 206/364 |
| 5,161,681 | 11/1992 | Kemp et al. | 206/364 |

FOREIGN PATENT DOCUMENTS

| | | | |
|---|---|---|---|
| 260312 | 4/1964 | Australia | 206/365 |
| 0071290 | 2/1983 | European Pat. Off. | |
| 0505579 | 9/1992 | European Pat. Off. | |
| 2024117 | 9/1971 | Germany | |
| 3101960 | 3/1991 | Japan | |
| 3-101960 | 10/1991 | Japan | |
| 938777 | 10/1963 | United Kingdom | 206/365 |

*Primary Examiner*—Jimmy G. Foster
*Attorney, Agent, or Firm*—Sughrue, Mion, Zinn, Macpeak & Seas

[57] ABSTRACT

A first object of the invention is to insure that medication filled syringe equipment can be kept sterile at all stages until use, is protected against malicious unauthorized use, can be packaged in a simpler way and can protect the medication to be in a stable form. A second object of the invention is to insure that an additional liquid such as an anesthetic, another medication in liquid form or a solubilizer can be aspirated by medication filled syringe equipment in an aseptic appropriate manner before injection. To attain these objects, the equipment of the invention comprises barrel 1, needle attaching portion 2 fitted with cap 11, plunger rod 22, and sealing device 31 as tube 32 of a heat-shrinkable film that is slipped over the area from the cap 11 through the barrel 1 to the basal head 23 of the plunger rod 22. The sealing device 31 is then caused to shrink thermally so that it will adhere closely to those members, thereby insuring that the barrel 1 filled with medication 5, plunger 21 and plunger rod 22 are isolated from ambient air. At the same time, the barrel 1 in which the medication 5 has been contained by the plunger 21 in a predetermined position in cooperation with the cap 11 is provided with marking 3 that is put within the area between the front and rear ends of the plunger 21 to indicate the limit beyond which the plunger 21 should not be withdrawn.

3 Claims, 1 Drawing Sheet

MEDICATION FILLED SYRINGE EQUIPMENT

TECHNICAL FIELD

This invention relates to medication filled syringe equipment that has the barrel filled with a given amount of medication and which can be distributed and stored intact until use.

BACKGROUND ART

Disposable syringe equipment which has a given amount of medication contained in the barrel is used extensively not only for saving the time required to have the medication transferred from an ampule into the barrel before injection but also for eliminating the potential hazard of infection with pathogenic bacteria and viruses due to the repeated use of the equipment.

Syringe equipment of this kind has the following basic construction: a cap is fitted on the needle attaching portion at the foremost end of the barrel and a plunger is inserted into the barrel from the rear end in such a way that a closed space is formed in front of the plunger, with a given amount of medication being contained in that space. Since one only need remove the cap and attach the needle to perform injection, the equipment has the advantage of providing great ease in handling.

The equipment, however, has a problem that originates from its simple construction; it adopts no closing means other than the cap which is detachably fitted on the needle attaching portion, so even if a malicious person ejects a portion of the medication or mixes it with a foreign matter or even replaces it with another medication, there is no way to check these acts as long as the cap is refitted.

A second problem with the equipment comes from the fact that it cannot be sterilized or disinfected just prior to use, which is in sharp contrast with another conventional type of syringe equipment that uses medications in ampules. Under the circumstances, it is necessary that the equipment of interest be distributed and stored in a sterilized atmosphere throughout the period from the filling of the medication in a sterile condition up to the time of actual use; to meet this need, the equipment must be wrapped with airtight packages and handled under strict control, this requiring cumbersome procedures.

To solve the first mentioned problem, the assignee previously proposed that the foremost end portion of the barrel and the cap are covered with a tubular continuous sealing device that is made of a heat-shrinkable film and which shrinks under heat to come into intimate contact with the outer peripheral surfaces of the foremost end portion of the barrel and the base portion of the cap, as well as the shoulder portion of the same (see the official gazette of Unexamined Published Japanese Utility Model Application Hei 3-101960).

According to this proposal, the sealing device prevents unauthorized removal of the cap and the plunger cannot be withdrawn since the medication filled space is closed (in vacuum). This offers the advantage of assuring freedom from anxiety for the user since he can verify that the syringe equipment has been properly sealed until use.

On the other hand, both the interior of the barrel at the basal end and the plunger rod remain exposed and provide areas for deposition of bacteria, viruses, as well as dirt or dust particles. To deal with this problem, the whole part of the syringe equipment must be wrapped with airtight packaging means. Thus, means for solving the aforementioned second problem is yet to be developed.

The sealing device proposed in Unexamined Published Japanese Utility Model Application Hei 3-101960, supra has another problem in that the cap must be shrunk sufficiently to assure strong adhesion to the outer peripheral surface of the barrel so that nobody can perform a misconduct by pulling the sealing device away from the barrel together with the cap and by then refitting it over the barrel. To meet this need, one may apply heat either at high temperatures for a short period or at comparatively low temperatures for a long period but, then, the medication in the barrel can potentially receive adverse thermal effects or the thermal expansion mismatch between the barrel, the plunger and the cap will cause gaps to form between these parts, which can potentially provide leaks for the medication.

If the medication in the barrel is a liquid of high viscosity, there is the need to use a fairly thick needle so that the medication of interest can be injected smoothly. To meet this need, it is often practiced that an anesthetic is aspirated into the barrel through the needle and injected into the patient, thereby alleviating the pain the patient may suffer during subsequent injection of the medication at the site of target.

A need also exists in certain cases for adding other substances than the medication of interest, as illustrated by the addition of another medication in liquid form immediately before the contained medication which is liquid form is injected or by the addition of a solubilizer just before the injection of the contained medication which is a powder, thereby rendering it in liquid form.

In these cases where another medication or the like that are in liquid form is (which are hereunder collectively referred to as the "additional liquid") to be added to the preloaded drug, the plunger must be moved in the direction for pulling it out of the barrel. However, with syringe equipment of the type contemplated by the invention which is filled with a given amount of medication, the barrel does not have graduations for reading the volume of the medication because there is no need to provide such graduations. Instead, the amount by which the plunger is withdrawn is measured visually to estimate the amount by which the additional liquid has been aspirated.

Under the circumstances, even if the plunger is designed to be longer than the predicted distance over which it is to be moved for aspirating the additional liquid, the foremost end of the plunger which has been located in a predetermined position may sometimes be moved backward of the position in which it was located at the time of filling in the medication if it is moved by a more-than-necessary large amount.

Those areas of the inside of the barrel which contact the plunger and the medication can be kept sterile throughout the period from the stages of distribution and storage up to the start of use. The area of the inside of the barrel which is backward of the plunger can also be kept sterile at the stages of distribution and storage since it is packed sterile by the sealing device; however, if the seal is opened to use the syringe, pathogenic bacteria and viruses may find the chance to adhere to the inner surfaces of that area. If the plunger is withdrawn up to the point where its foremost end reaches the area contaminated by the deposits of pathogenic bacteria and viruses, the medication will contact them and the patient can potentially be infected by the injection of the contaminated medication.

Thus, the first problem to be solved by the present invention is that the conventional syringe equipment which has a cap fitted on the needle attaching portion at the foremost end of the barrel and which has a plunger fitted in the barrel from the rear end to a predetermined position, with a medication being contained in the barrel, has had no sealing means available that can be applied easily without involving the aforementioned disadvantages, thereby attaining both purposes of preventing the malicious unauthorized use of the syringe and keeping it sterile at all stages up to its use.

The second problem to be solved by the present invention is that with said conventional syringe equipment, even the use of a plunger of considerable length does not eliminate the potential risk that if a medication in liquid form other than the one that is preliminarily contained in the barrel is aspirated for injection, pathogenic bacteria or viruses may contaminate the medication which is eventually administered to the patient.

Therefore, the first object of the invention is to insure that medication filled syringe equipment can be kept sterile at all stages until use, is protected against malicious unauthorized use, can be packaged in a simpler way and can protect the medication to be in a stable form.

The second object of the invention is to insure that an additional liquid such as an anesthetic, another medication in liquid form or a solubilizer can be aspirated by medication filled syringe equipment in an aseptic appropriate manner before injection.

SUMMARY OF THE INVENTION

The first object of the invention can be attained by medication filled equipment that has a cap fitted on the needle attaching portion at the foremost end of the barrel and which has a plunger fitted in the barrel from the rear end to a predetermined position, with a predetermined dose of a medication being contained in the barrel, characterized in that said cap, said barrel, as well as the plunger rod projecting backward of the barrel and its basal head are covered with a tubular sealing device that is made from a heat-shrinkable film and which has been shrunk under heat so that it adheres closely to the surfaces of those members.

In a preferred embodiment, the basal head of the plunger rod has a flange at the front end and a flared portion that increases in diameter from said flange backward, with the rear end of said sealing device being positioned in registry with said flared portion.

Having this construction, the syringe equipment of the invention is covered airtightly in all areas, except the foremost end portion of the cap and the rear end of the basal head of the plunger rod, by means of the sealing device that has been caused to adhere closely to those areas as a result of thermal shrinkage, whereby the syringe equipment can be distributed and stored with both the inside of the barrel at the basal end and the plunger rod being effectively isolated from ambient atmosphere. To use the syringe equipment, the sealing device is torn apart in the right and left directions so that it can be removed from the barrel.

To attain the second object of the present invention, the syringe equipment is preferably provided on the barrel with a marking that is within the area between the front and rear ends of the plunger as located at a predetermined position in the barrel and which indicates the limit beyond which the plunger should not be withdrawn. This arrangement insures that when a medication is aspirated through a needle that is attached to the barrel after the sealing device and the cap have been removed, the plunger can positively be withdrawn to such a point that its front end does not go beyond the marking. As a result, the medication can be injected into the patient substantially aseptically without contacting any part of the inside of the barrel that is backward of the rear end of the plunger which has been located in the predetermined position.

DETAILED DESCRIPTION OF THE INVENTION

Embodiments

Figure 1:
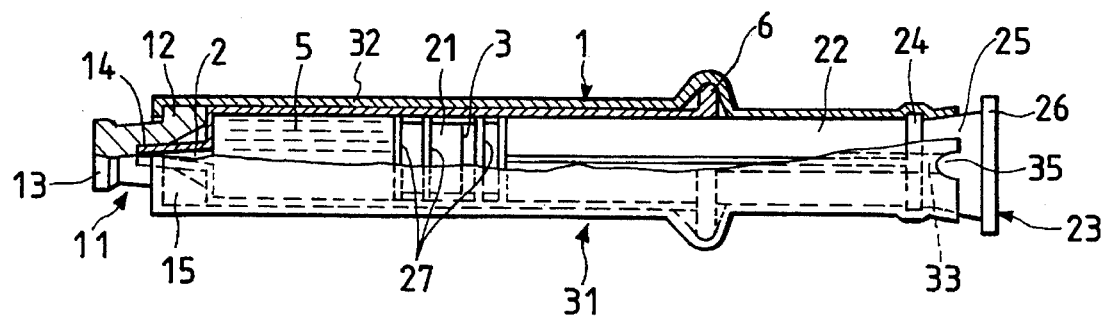
FIG. 1 is a front view showing, with part taken away, syringe equipment that is covered with a sealing device according to an embodiment of the invention.

Embodiments of the present invention are described below with reference to the accompanying drawings. Shown in FIG. 1 is the barrel of a syringe which is generally indicated by numeral 1. A needle attaching portion 2 projects from the foremost end of the barrel 1. A cap 11 is fitted over the needle attaching portion 2. The cap 11 which is typically formed of butyl rubber has a base 12 at the basal end, a flange-like grip 13 at the front end and an insertion hole 14 that is open in the face at the basal end. The base 12 is substantially of the same diameter as the outside diameter of the barrel 1. The cap 11 is fitted in such a way that the needle attaching portion 2 is pressed into the insertion hole 14 and that the face at the basal end of the base 12 is in intimate contact with the face at the front end of the barrel 1.

A plunger 21 typically formed of butyl rubber is fitted into the barrel 1 from the rear end to a predetermined position in a liquid-tight fashion, with a predetermined amount of medication 5 being contained in the closed space that is formed by the cap 11 and the plunger 21 in an area closer to the front end of the barrel 1.

The plunger 21 is secured to the foremost end of a plunger rod 22 by, for example, screw fitting. To secure enhanced sealing of the medication 5, an annular rib 27 that is in intimate contact with the inner surface of the barrel 1 is provided at the front end, the rear end and in the middle of the plunger 21 and, at the same time, the plunger is designed to have a considerable length. It should, however, be noted that this is not the sole example of the construction that can be adopted to secure effective sealing of the medication 5. It should also be noted that the plunger is designed to be longer than the distance over which it must be displaced to aspirate an additional liquid. Marking 3 in the form of a colored fine line extending circumferentially is provided on the surface of the barrel 1 in the area between the front and rear ends of the plunger and this indicates the limit beyond which the plunger 21 should not be withdrawn to aspirate the additional liquid.

The plunger rod 22 extends backward the barrel 1 and has a basal head 23 at the rear end. The basal head 23 is of such a construction that it comprises, in the order written, a flange 24 slightly larger in diameter than the plunger rod 22, a flared portion 25 that is of substantially the same diameter as the plunger rod 22 at the front end and which increases in diameter toward the rear end, and a flange-like pressing portion 26.

A sealing device 31 which is the most important feature of the invention is described below with reference to FIG. 2. The sealing device comprises a tube 32 and a tear tape 33. The tube 32 is formed of a transparent heat-shrinkable film that is made from a synthetic resin such as poly(vinyl chloride), polystyrene, polypropylene, poly(vinylidene chloride), polyamide or polyethylene, that is of substantially the same length as the overall length of the syringe equipment under consideration and which is slightly larger in diameter than a rear flange 6 provided around the barrel 1. The tear tape 33 is attached by bonding to the inner surface of the tube 32 from one end to the other in the longitudinal direction. The tube 32 is subjected to preliminary drawing so that it will shrink by given amounts in both longitudinal and circumferential directions upon application of heat.

To construct the sealing device 31, an elongated heat-shrinkable film to which the elongated tear tape 33 has been attached is cut to a given length and rolled on itself to form the tube 32. One end of the tear tape 33 protrudes beyond the end face of the tube 32 to serve as a seal opening start lug 34 whereas the other end of the tape 33 is formed as a concave 35 to ensure complete rip of the tube.

Figure 2:
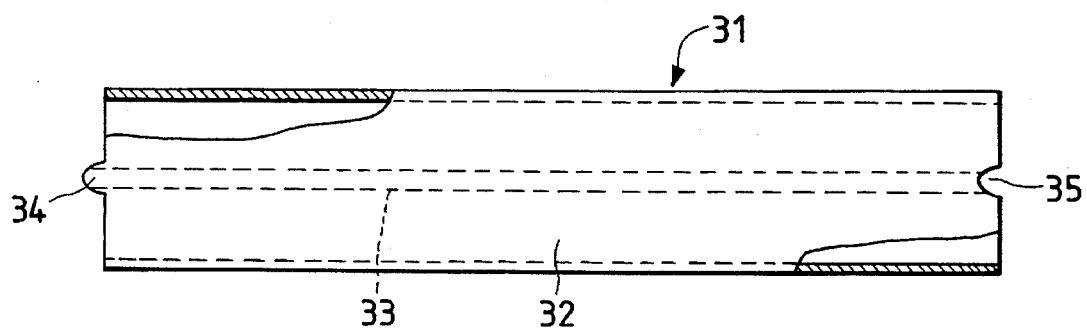
FIG. 2 is a front view showing, with part taken away, the sealing device.

The seal opening start lug of the tape which is attached to the sealing device 31 need not be a projection from one end of the tube 32 as indicated by 34 in FIG. 2. Alternatively, a cut may be made on both sides of the tape as attached to one end of the tube 32, thereby providing a structure that permits easy grip of the seal opening start lug and which ensures complete rip of the tube.

If desired, the position of the seal opening start lug and the direction of its opening may be indicated expressly. To this end, one or more markings (e.g., arrows) that designate the position and direction of seal opening may be provided on the tear tape or in the area of the tube to which the tear tape has been attached.

To place the sealing device 31 over the barrel 1, it is first positioned in such a way that the seal opening start lug 34 is in registry with the cap 11 and then it is slipped over the barrel to extend from the cap 11 through the plunger rod 22 backward of the rear flange 6 up to the basal head 23. When the sealing device is heated by a suitable means such as rf induction, ir heater, impulse heat sealing or a hot air stream, it shrinks and the foremost end is bent toward the center of the barrel along the shoulder 15 of the cap 11 while the remainder extends along the base 12 of the cap 11, the barrel 1, the rear flange 6 and the backward projection of the plunger rod 22, with the rear end reaching the neighborhood of the rear end of the flared portion 25 of the basal head 23. The sealing device 31 thus shrunk adheres closely to these members and parts of the syringe equipment under consideration.

In the embodiment described above, the cap 11 is fitted over the needle attaching portion 2 in such a way that the latter is pressed into the insertion hole 14 in the cap 11 and, at the same time, the front end face of the barrel 1 is held in intimate contact with the basal end face of the cap base 12 which is of substantially the same diameter as said front end face. Because of these two structural features, the cap 11 closes the needle attaching portion 2 with a high degree of airtightness. As a next feature, the sealing device 31 has its front end placed in intimate contact with the shoulder 15 of the cap and this further enhances the airtightness of the needle attaching portion 2. In addition, the rear end of the sealing device 31 is placed in intimate contact with the flared portion 25 of the basal head 23, whereby not only the inside of the barrel 1 that is backward of the plunger 21 and which is closer to the basal end but also the plunger rod 22 is surrounded with an airtight atmosphere to prevent the deposition of contaminants such as pathogenic bacteria, viruses and dirt or dust particles.

Therefore, if the filling of the barrel 1 with medication 5 in a sterile atmosphere is accompanied by slipping the sealing device 31 over the barrel in the same sterile atmosphere and shrinking it thermally so that it comes in intimate contact with the barrel, any part of the syringe that may come in contact with the medication 5 can be kept invariably sterile by means of the sealing device 31. As a result, the overall syringe package for distribution and storage can be either simplified or totally omitted.

As already mentioned, the rear end portion of the sealing device 31 is held in intimate contact with the flared portion 25 of the basal head 23. Since the flared portion 25 increases in diameter toward the rear end of the head, the sealing device 31 will, upon shrinking, adhere firmly to the barrel as it approaches the rear edge, thereby assuring further enhanced airtightness. The concave 35 in the sealing device 31 is located in registry with the flared portion 25 and, hence, will not impair the airtightness of this area.

It should also be noted that as long as the sealing device 31 is allowed to adhere firmly to the cap 11 and the basal head 23, it need not be brought into as strong intimate contact with the area intermediate between those members. Hence, one only need apply heat of comparatively low temperatures for a short period of time to the intermediate area and this is effective for not only avoiding any adverse thermal effects on the medication 5 but also eliminating the concern over possible leakage of the medication due to the thermal expansion mismatch between various parts of the syringe.

It should also be noted that the sealing device 31 covers the whole part of the barrel 1, as well as the entire part of the plunger rod 22 except a portion of the basal head 23; hence, the sealing device 31 also has cushioning and reinforcing capabilities in that it reduces the chance of breakage upon impact that may be caused by, for example, accidental drop while, at the same time, the glass-made barrel 1 is rendered shatterproof to insure utmost safety in handling. As a further advantage, moving the plunger rod 22 is practically impossible and it is protected against any unauthorized attempt at pushing or pulling, whereby the medication 5 can be contained in the closed space in a stable manner.

To use the syringe equipment, the seal opening start lug 34 of the tear tape 33 is held with fingertips or tweezers and pulled backward, whereby the tube 32 is torn apart along the tape 33; thereafter, the cap 11 is removed, a needle is attached to the barrel 1 and, if necessary, the plunger 21 is withdrawn up to such a point that its front end does not go beyond the marking 3, thereby aspirating an additional liquid such as an anesthetic to be injected.

Figure 3:
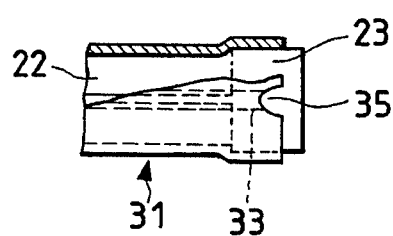
FIG. 3 is a partial front view showing, with part taken way, syringe equipment according to another embodiment of the invention.

In the embodiment shown in FIG. 1, the basal head 23 of the plunger rod 22 is provided with the flared portion 25. Alternatively, the basal head 23 may be shaped in the form of a thick disk as shown in FIG. 3; an advantage of this case is that when the sealing device 31 is caused to shrink, it can be fitted over the basal head 23 assuring good airtightness with the concave 35 being positioned on the outer circumference of the head.

The sealing device 31 may be provided with perforations from one end to the other in the longitudinal direction so that it can be torn apart along the line of those perforations. However, from the viewpoint of airtightness, the tear tape 33 is preferred over the perforations.

Figure 4:
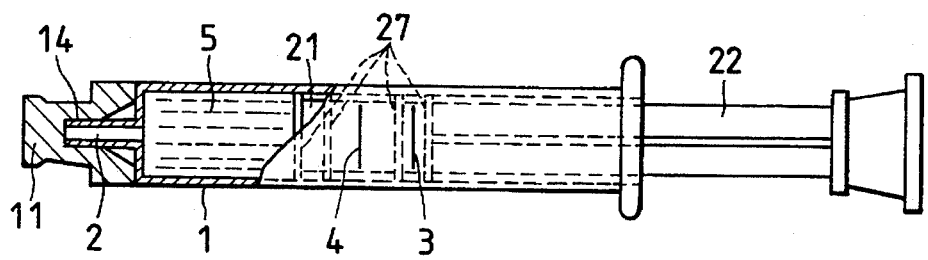
FIG. 4 is a front view showing, with part taken away, syringe equipment according to yet another embodiment of the invention (the sealing device not shown) in which a marking for indicating the limit beyond which the plunger should not be withdrawn, as well as an auxiliary marking are provided on the barrel.

FIG. 4 shows medication filled syringe equipment according to another embodiment of the present invention. The second embodiment is described below more specifically with reference to FIG. 4.

The plunger 21 is designed to be longer than the distance over which it is to be displaced for aspirating an additional liquid such as an anesthetic, medication or solubilizer that are different from the medication 5 already contained in the barrel 1. The plunger 21 has an annular rib 27 formed not only at the front and rear ends by also in the intermediate area in such a way that the ribs are in intimate contact with the inner surface of the barrel 1, thereby working as sealants.

With the plunger 21 being located in a predetermined position, the barrel 1 has marking 3 provided within the area between the front and rear ends of the plunger 21; the marking 3 is a colored fine line extending in the circumferential direction for the purpose of indicating a maximum volume of the additional liquid that can be aspirated, namely, the limit which should not be exceeded by the front end of the plunger 21 being withdrawn. In other words, the marking 3 warns the user that the following two possibilities will occur if, with the cap 11 being removed and a needle attached for aspirating an additional liquid, the plunger 21 is withdrawn up to a point backward of the marking 3: first, the additional liquid may be aspirated in an excessive amount that can reduce the efficacy of the contained medication 5 or cause adverse effects on the patient; second, the medication 5 may be contaminated by pathogenic bacteria, viruses or dust or dirt particles that can potentially adhere to the inner surface of the barrel 1 in those areas which are backward of a position a given distance away from the rear end of the plunger 21.

Hence, the marking 3 has the added advantage that a medication such as an anesthetic the dose of which must be adjusted in accordance with the condition of the patient can be administered in the correct dose since the amount of aspiration can be known by the distance between the marking 1 and the front end of the plunger 21 being withdrawn. The auxiliary marking 4 may or may not be provided on the syringe equipment of the present invention and its function is to indicate the standard or minimum volume of the additional liquid to be aspirated; hence, by withdrawing the plunger 21 with reference to the auxiliary marking 4 in accordance with the condition of the patient, the appropriate volume of the additional liquid can be aspirated and injected into the patient. The auxiliary marking 4 need not be one in number and two or more auxiliary markings may be provided.

It should be noted here that the marking 3 and the auxiliary marking 4 are in no way limited to fine lines and may be comprised of any other symbols such as arrows or dots. Needless to say, those markings may be accompanied by indications of their meanings such as a statement to the effect that they represent the limit beyond which the plunger 21 should not go, or by characters that indicate the volume or other parameters.

Industrial Applicability

Thus, with the syringe equipment of the invention in which the tubular sealing device slipped over the area from the cap to the basal head is thermally shrunk to adhere to those parts, not only the inside of the barrel in a portion closer to the basal end but also the plunger rod is protected sterile as they are isolated from ambient air throughout the period from the filling with a medication up to the start of use, whereby the syringe can be used hygienically even after it is distributed and stored with a simplified package or without a package at all. Furthermore, the user will not have any anxiety since no unauthorized person can remove the sealing device, adulterate the medication in the barrel and refit the sealing device. In addition, the sealing device can be brought into intimate contact with the necessary parts of the syringe by causing it to shrink thermally without any adverse thermal effects on the medication or any leakage of the latter and this guarantees high reliability in the quality of the equipment. Another advantage of the invention is that the sealing device capable of protection from impacts not only assures enhanced safety but also secures the plunger rod in such a way that the contained medication can be kept in a stable condition.

If desired, a marking for indicating the limit beyond which the plunger as inserted to a given position within the medication filled barrel should not be withdrawn may be provided on the barrel surface within the area between the front and rear ends of the plunger. An advantage of this arrangement is that when an additional liquid such as a medication other the contained one, an anesthetic or a solubilizer is aspirated for injection, the chance of retracting the plunger to such a point that its front end is farther backward of the initial rear end (i.e., when it was located in the given position) is eliminated to secure utmost safety by insuring that no pathogenic bacteria, viruses and dirt or dust particles on the inner surface of the barrel will contaminate the additional liquid being injected. The marking offers another advantage in that the additional liquid can be aspirated in an appropriate volume and allowed to exhibit the intended efficacy or it can be injected into the patient without taking the risk of affecting him adversely.

I claim:

1. A medication filled syringe equipment comprising a barrel having a foremost end and a rear end; a needle attaching portion at said foremost end of said barrel; a cap fitted on said needle attaching portion; a plunger fitted in said barrel from said rear end of said barrel to a predetermined position in said barrel; and a plunger rod connected to said plunger and having a portion projecting backward beyond the rear end of said barrel and terminating in a basal head; with a predetermined dose of a medication being contained in said barrel, wherein said cap, said barrel, as well as the portion of said plunger rod projecting backward beyond said barrel and said basal head of said plunger rod are covered with a tubular sealing device including a front end and a rear end and which is made from a heat-shrinkable film and which has been shrunk under heat so that said sealing device adheres closely to an outer surface of each of said cap, said barrel, the portion of said plunger rod projecting backward beyond said barrel and said basal head of said plunger rod.

2. The medication filled syringe equipment according to claim 1, wherein said basal head of said plunger rod includes a front end having a flange and a flared portion that increases in diameter from said flange backward, with the rear end of said sealing device being positioned in registry with said flared portion.

3. The medication filled syringe equipment according to claim 1, wherein said plunger has a front end and a rear end which define an area therebetween, and wherein said barrel is provided with a marking that is within the area between the front end and the rear end of said plunger as located at the predetermined position in said barrel and which indicates a limit beyond which said plunger should not be withdrawn.

* * * * *